US00PP20682P2

(12) United States Plant Patent
Rinck

(10) Patent No.: US PP20,682 P2
(45) Date of Patent: Jan. 26, 2010

(54) ***PENNISETUM* PLANT NAMED 'IVORY FOUNTAIN'**

(50) Latin Name: *Pennisetum setaceum*
Varietal Denomination: Ivory Fountain

(76) Inventor: Michael C. Rinck, 19825 SR 44, Eustis, FL (US) 32736

( * ) Notice: Subject to any disclaimer, the term of this patent is extended or adjusted under 35 U.S.C. 154(b) by 0 days.

(21) Appl. No.: 12/291,651

(22) Filed: Nov. 12, 2008

(51) Int. Cl.
*A01H 5/00* (2006.01)

(52) U.S. Cl. ..... Plt./384
(58) Field of Classification Search ..... Plt./384
See application file for complete search history.

*Primary Examiner*—Annette H Para
(74) *Attorney, Agent, or Firm*—Penny J. Aguirre

(57) ABSTRACT

A new cultivar of *Pennisetum setaceum* named 'Ivory Fountain', characterized by its racemes (seed heads) that emerge white and tinged with rose-purple and fade to white as they mature, its year around free flowering habit, its arching leaves, its height of 48 to 54 inches in bloom, its sterile seeds, and its vigorous growth habit.

2 Drawing Sheets

Botanical classification: *Pennisetum setaceum.*
Varietal denomination: 'Ivory Fountain'.

BACKGROUND OF THE INVENTION

The present invention relates to a new and distinct cultivar of *Pennisetum setaceum* and will be referred to hereafter by its cultivar name, 'Ivory Fountain'. 'Ivory Fountain' represents a new cultivar of Purple fountain grass, a warm-season, ornamental grass grown for container and landscape use.

The Inventor discovered and selected the new cultivar, 'Ivory Fountain', as a culm sport of *Pennisetum setaceum* 'Rubrum' (not patented) in a container at his nursery in Eustis, Florida in September of 2007.

Asexual reproduction of the new cultivar was first accomplished by in vitro propagation in Eustis, Florida in November of 2007 by the Inventor. The characteristics of this cultivar have been determined to be stable and are reproduced true to type in successive generations.

SUMMARY OF THE INVENTION

The following traits have been repeatedly observed and represent the characteristics of the new *Pennisetum* as observed for a period of one year as grown in Eustis, Fla. These attributes in combination distinguish 'Ivory Fountain' from all other selections of *Pennisetum* known to the Inventor.

1. 'Ivory Fountain' blooms with racemes (seed heads) that emerge white and tinged with rose-purple and fade to white as they mature.
2. 'Ivory Fountain' exhibits green leaves than are wider and more arching than the species, *Pennisetum setaceum*.
3. 'Ivory Fountain' reaches a foliage height of 36 to 48 inches with racemes (seed heads) reaching 48 to 54 inches in height.
4. 'Ivory Fountain' forms sterile seeds.
5. 'Ivory Fountain' is free flowering with racemes produced year around.
6. 'Ivory Fountain' exhibits a vigorous growth habit.

In comparison to the parent plant, *Pennisetum setaceum* 'Rubrum', 'Ivory Fountain' differs in having green foliage rather than red, in being shorter in height by 6 to 8 inches, and in having emerging racemes that are about 20% tinged in rose-purple whereas the racemes of 'Rubrum' are about 80% tinged with rose-purple. In comparison to the species, *Pennisetum setaceum*, 'Ivory Fountain' has leaves that are slightly wider and more arching, has racemes that are rose-purple tinged, is taller in height, and produces sterile seeds.

BRIEF DESCRIPTION OF THE DRAWING

The accompanying colored photographs illustrate the overall appearance and distinct characteristics of a one year-old plant of the new *Pennisetum* as grown in a garden in Eustis, Fla.

The photograph in FIG. 1 provides a view of the habit in bloom of 'Ivory Fountain'.

Figure 1:
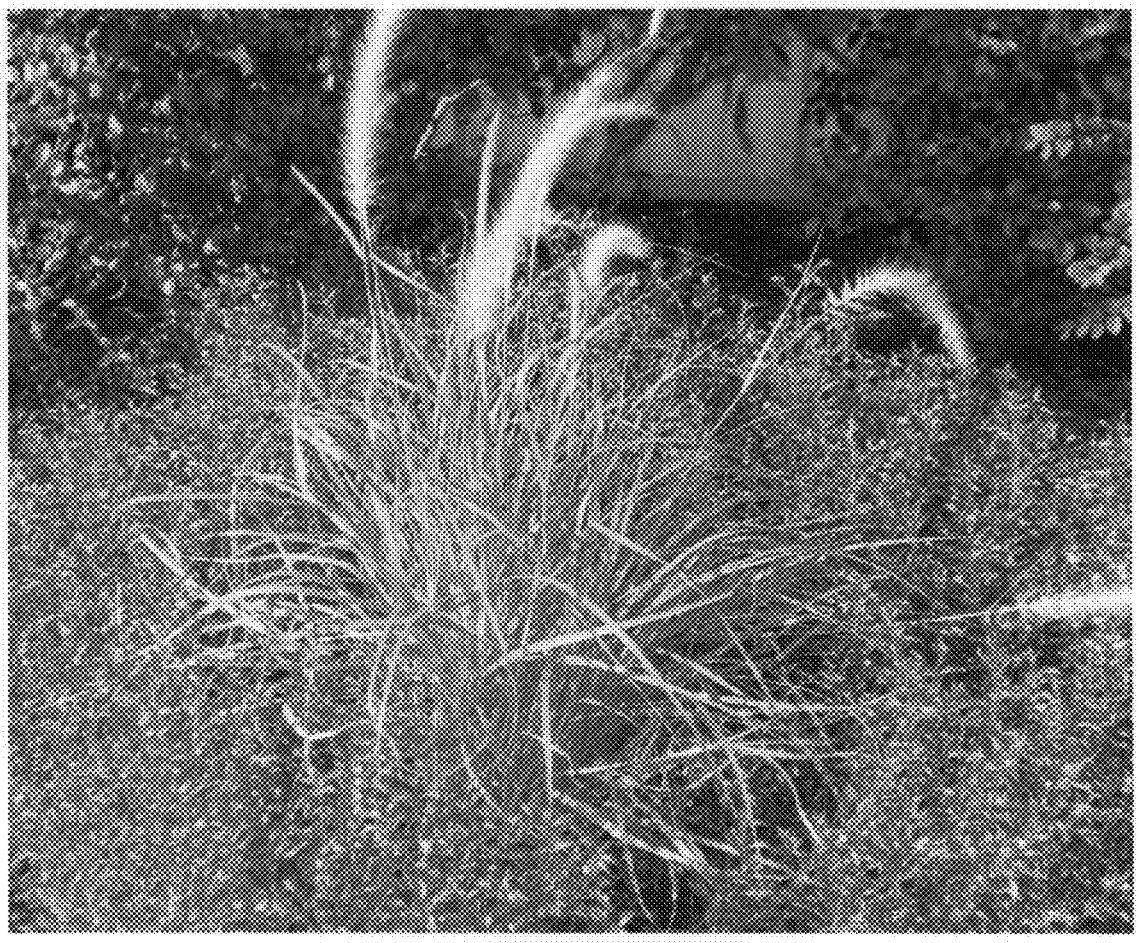
Figure 2:
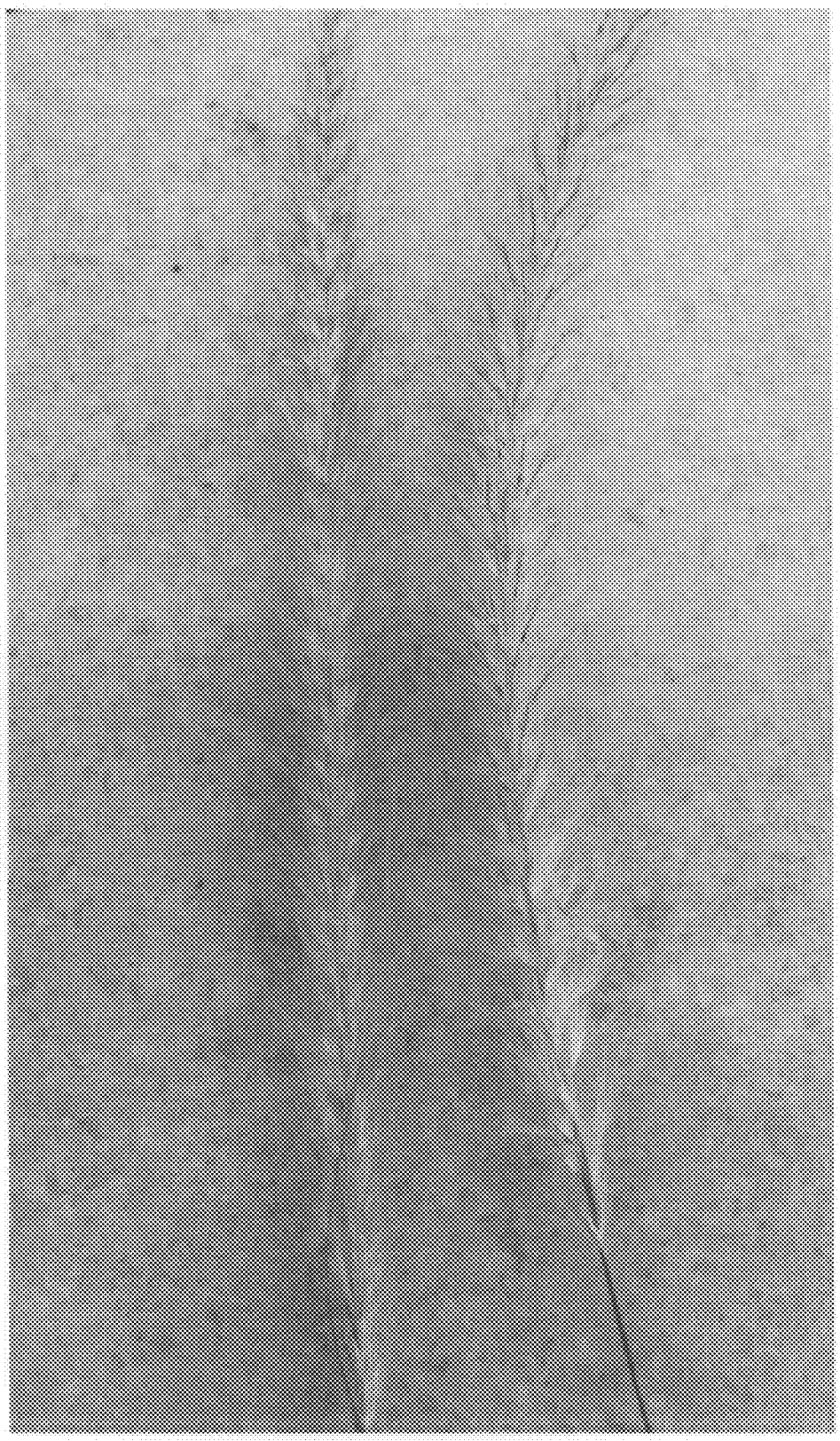

The photograph in FIG. 2 provides a view of a newly emerged inflorescence on the left and a mature inflorescence on the right.

The colors in the photograph may differ slightly from the color values cited in the detailed botanical description, which accurately describe the colors of the new *Pennisetum.*

DETAILED BOTANICAL DESCRIPTION

The general observations and descriptions describe seven month-old plants as grown outdoors in a one-gallon containers in Eustis, Fla. The new *Pennisetum* has not been observed under all possible environmental conditions. The phenotype may vary somewhat with variations in temperature, daylength, light intensity, soil types, and water and fertility levels without, however, any variance in genotype. The color determinations are in accordance with the 2007 R.H.S. Colour Chart of The Royal Horticultural Society, London, England, except where general color terms of ordinary dictionary significance are used.

General description:

*Blooming period.*—Blooms year around once initial racemes are formed.

*Plant habit.*—Herbaceous, clump-forming, ornamental grass with an upright culms and arching leaf blades.

*Height and spread.*—Reaches a foliage height of 36 to 48 inches with plumes (seed heads) reaching 48 to 54 inches in height and a spread of about 24 inches.

*Hardiness.*—U.S.D.A. Zones 9 to 10.

*Diseases and pests.*—*Pennisetum setaceum* has no known disease resistance or pest problems.

*Root description.*—Fine, fibrous, and numerous.

Growth and propagation:

*Propagation.*—Culm division and tissue culture (preferred).

*Time required for root initiation.*—Roots appear ex vitro in 7 to 10 days when grown in a greenhouse at 650° to 80° F.

*Time required for root development from a single division.*—1-inch liners fully develop in a 6-inch container with 8 weeks under greenhouse conditions.

*Growth rate.*—Vigorous.

Culm (stem) description:

*General.*—Cylindrical, enclosed by leaf sheaths.

*Culm aspect.*—Held nearly erect.

*Culm color.*—144A to 144C (comprised of leaf sheaths).

*Culm size.*—Average of 44 cm in length and an average of 3.5 mm in width.

*Culm surface.*—Glabrous and slightly satiny.

*Internode length.*—Average of 4.2 cm.

Foliage description:

*Leaf shape.*—Linear.

*Leaf division.*—Simple.

*Leaf base.*—Sheathed.

*Leaf apex.*—Attenuate.

*Leaf aspect.*—Emerging leaves are erect, leaf blades diverge from leaf sheath at ligule at about a 45° angle from center of culm then gently arch downward when mature, blades are flat and recessed at mid rib.

*Leaf venation.*—Parallel, mid rib is recessed on upper surface, color matches the color of the leaf blades on upper and lower surface.

*Leaf margins.*—Entire and finely scabrous to touch.

*Leaf persistence.*—Foliage dries with new foliage continuously produced.

*Leaf attachment.*—Sheathed, leaf is sheathed from the base of culm and the blade extends out from the culm at a ligule.

*Ligule.*—Average of 1.5 mm in width, extends length of leaf blade, color is 155B, membranous with fine short hairs on margin.

*Leaf size.*—Average of 36 cm in length and 7 mm in width when mature; narrower at culm attachment and tapering to a fine point at apex.

*Leaf surface.*—Glabrous and dull to a slight satiny sheen on upper and lower surface.

*Leaf number.*—Average of 7 leaves per culm.

*Leaf arrangement.*—Alternate, 2 ranked.

*Leaf color.*—Color between 137B and 144A on upper and lower surface, dries to 161A in color.

Flower description:

*General description.*—Inflorescence is a plumose raceme terminating from each culm, emerging upright and then gradually cascading outward, comprised of 1 to 2 spikelets surrounded by an involucre of bristles.

*Lastingness of inflorescence.*—Racemes dry but remain persistent.

*Fragrance.*—None.

*Raceme size.*—Mature to an average of 24 cm in length and 3.5 cm in width.

*Raceme color.*—Emerge a blend of 144A and 157A (spikelet portion) covered with spikes 155A and tinged with N77C, as the raceme matures, the N77C tinge is lost and the overall color is 155A (the overall raceme color is primarily determined by the bristles).

*Spikelet description.*—Single and arranged in whorls on rachis, average of 1.2 cm (3 cm including bristles) and 1.5 mm in width (3.5 cm including bristles), glumes; 2, membranous, transparent and 145D in color with veins 144A, about 6 mm in length and 1.5 mm in width, palae; about 5 mm in length and 1.5 mm in length, lemma and palea; translucent with tint of 145D, equal in size and about 6 mm in length and 1 mm in width, bristles; attached to base of spikelet, up to 2.5 cm in length, unequal in length, 155A and tinged with N77C and changing to 155A.

*Rachis.*—About 24 cm in length and 1 mm in width, 144A in color, oval in shape, surface is finely ridged with sparse hairs.

*Reproductive organs.*—Pistil; 1 with 2 plumose stigmas about 7 mm in length, 0.4 mm in width and 158A in color, stamens; 3, about 2.5 mm in length, 0.3 mm in width and 163C in color, pollen; not visible.

*Seed.*—Sterile.

It is claimed:

1. A new and distinct cultivar of *Pennisetum* plant named 'Ivory Fountain' as herein illustrated and described.

* * * * *